United States Patent [19]

Gaetani et al.

[11] 4,409,379

[45] Oct. 11, 1983

[54] COPOLYMERIZATION PROCESS INITIATED WITH BIS (4-TERT. BUTYL CYCLOHEXYL) PEROXYDICARBONATE AND AEROSOL HAIR LACQUER CONTAINING THE COPOLYMER SO PRODUCED

[75] Inventors: Quintino Gaetani, Bondy; Bernard Jacquet, Antony; Claude Mahieu, Paris; Christos Papantoniou, Montmorency, all of France

[73] Assignee: L'Oreal, Paris, France

[21] Appl. No.: 288,157

[22] Filed: Jul. 29, 1981

Related U.S. Application Data

[63] Continuation of Ser. No. 83,653, Oct. 11, 1979, abandoned.

[30] Foreign Application Priority Data

Oct. 26, 1978 [FR] France ............................ 78 30462

[51] Int. Cl.³ .......................... C08F 4/34; A61K 7/11
[52] U.S. Cl. ............................ 526/230.5; 424/47; 424/70; 526/317
[58] Field of Search ..................................... 526/230.5

[56] References Cited

U.S. PATENT DOCUMENTS

| | | | |
|---|---|---|---|
| 3,528,956 | 9/1970 | Gerritsen | 526/230.5 |
| 4,048,192 | 9/1977 | Stoll | 526/230.5 |
| 4,129,711 | 12/1978 | Viout | 526/286 |
| 4,282,203 | 8/1981 | Jacquet | 424/47 |

*Primary Examiner*—C. A. Henderson
*Attorney, Agent, or Firm*—Cushman, Darby & Cushman

[57] ABSTRACT

Vinyl acetate and an unsaturated acid are copolymerized in the presence of bis (4-tert. butyl cyclohexyl) peroxydicarbonate. The resulting copolymer which exhibits improved aerosol propellant solubility characteristics is employed in aerosol hair lacquer compositions.

6 Claims, No Drawings

COPOLYMERIZATION PROCESS INITIATED WITH BIS (4-TERT. BUTYL CYCLOHEXYL) PEROXYDICARBONATE AND AEROSOL HAIR LACQUER CONTAINING THE COPOLYMER SO PRODUCED

This is a continuation of application Ser. No. 083,653 filed Oct. 11, 1979, now abandoned.

The present invention relates to a new process for preparing copolymers which are particularly useful in the production of aerosol hair lacquer compositions.

The present invention also relates to an aerosol hair lacquer composition containing at least one copolymer prepared in accordance with the process of the present invention.

BACKGROUND OF THE INVENTION

Numerous copolymers conventionally used to produce aerosol hair lacquer compositions contain both units derived from vinyl acetate and units derived from an unsaturated acid such as, principally, crotonic acid. Representative of such copolymers are the 90–10 vinyl acetate-crotonic acid copolymer, vinyl acetate-crotonic acid-vinyl stearate copolymer, vinyl acetate-crotonic acid-allyl stearate copolymer and vinyl acetate-allyloxyacetic acid-allyl stearate copolymer.

The use of these copolymers in aerosol hair lacquer compositions is disclosed, particularly, in French Pat. Nos. 1,517,743 and 1,580,545.

The use of these copolymers in aerosol hair lacquer compositions requires the use of an alcohol so as to obtain good stability of the copolymer when there is introduced into the aerosol container an aerosol propellant which generally comprises a fluorinated hydrocarbon and principally a mixture of trichlorofluoromethane (Freon 11) and dichlorodifluoromethane (Freon 12), a mixture of hydrocarbons (propane, butane, isobutane and the like), dimethylether, carbon dioxide or the like.

Since the alcohol which can be either ethanol or isopropanol constitutes a less than desirable component in an aerosol hair lacquer composition, attempts have been made to reduce the alcohol content by replacing a portion thereof with a third solvent.

However, in this situation, it has always been necessary to use relatively large amounts of alcohol so as to obtain good spraying and good drying speed of the lacquer on the hair.

DETAILED DESCRIPTION OF THE INVENTION

It has now surprisingly been found that by preparing copolymers having vinyl acetate units and unsaturated acid units in the presence of a particular type of copolymerization initiator, it is possible to reduce the alcohol content due to the improved solubility of the resulting copolymers in the aerosol propellant.

The present invention thus relates to a new process for preparing a copolymer, useful particularly in the preparation of aerosol hair lacquer compositions, having the general formula:

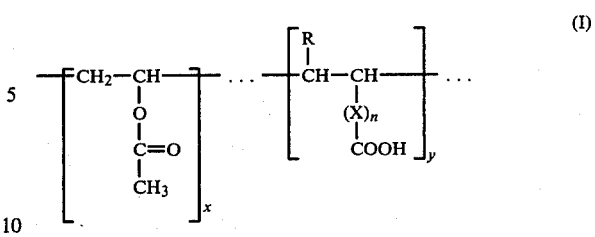

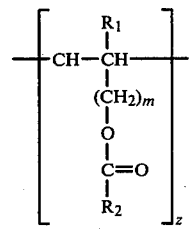

wherein
R represents hydrogen or methyl,
n is 0 or 1,
X represents a divalent radical selected from the group consisting of $-CH_2-$, $-CH_2O-CH_2-$ and $-CH_2-O-(CH_2)_2-$.
m is 0 or 1,
when m is 0, $R_1$ represents hydrogen and $R_2$ represents linear or branched alkyl having 2–21 carbon atoms, and
when m is 1, $R_1$ represents hydrogen or methyl and $R_2$ represents linear or branched alkyl having 1–21 carbon atoms,
x represents 60–95, and preferably 85–95, weight percent,
y represents 5–15 weight percent and
z represents from 0 to 25 weight percent, with $x+y+z$ being equal to 100 weight percent, said process comprising copolymerizing the monomeric constituents of said copolymer in the presence of bis(4-tert.-butyl cyclohexyl)peroxydicarbonate as a polymerization initiator.

The polymers obtained by this process which includes the use of this polymerization initiator have proven to exhibit a much better solubility in an aerosol propellant which, accordingly, has permitted the production of aerosol hair lacquer compositions containing reduced amounts of alcohol.

Because of this reduction in alcohol content, aerosol hair lacquer compositions made with copolymers obtained in accordance with the present invention are less costly while at the same time they exhibit excellent properties including, principally, very good hair lacquering power.

Further, it has now been found that by using the copolymers prepared by the process of the present invention, it is possible to achieve, even though using lesser amounts thereof, a lacquer power or "static holding" characteristic essentially identical to that achieved with a comparable polymer prepared with the aid of a conventional initiator such as, for example, benzoyl peroxide or azo bis-isobutyronitrile.

While the exact reasons leading to the present attainment of polymers exhibiting improved aerosol propellant solubility characteristics have not yet been determined, it is thought that the bis(4-tert. butyl cyclohexyl)peroxydicarbonate, the decomposition of which is quite rapid, may have some influence even on the structure of the resulting polymers.

However, this rapid decomposition does not appear to be the only determining factor since studies have also shown that other polymerization initiators which also exhibit rapid decomposition do not provide comparable results, that is, improved solubility in, for example, a propellant mixture of Freon 11 and Freon 12.

The copolymerization reaction of the process of the present invention can be effected in accordance with known procedures, i.e. in mass, in suspension in an inert solvent, in solution in a solvent or in an emulsion.

In accordance with a preferred embodiment, the polymerization reaction is carried out in suspension in water in the presence of a protective colloid or suspension agent such as, for example, polyvinyl alcohol, crosslinked polyacrylic acid, the product known under the trade name of "Cellosize WP-09" and the like. The use of such a component yields, at the end of the reaction, the polymer in pearl form.

It is also possible to employ yet another polymerization process which comprises preparing, initially, a mixture of the monomers to be copolymerized and the aforementioned polymerization initiator. This mixture is then slowly introduced into the polymerization reactor. In accordance with this embodiment of the invention, the mixture of monomers and polymerization initiator can be introduced as such or diluted in a solvent in the polymerization reactor containing, optionally, a certain amount of solvent.

Whatever polymerization procedure is employed, the amount of bis(4-tert.-butyl cyclohexyl)peroxydicarbonate is generally between 0.2 and 5 weight percent based on the total weight of the monomers to be copolymerized.

The temperature of the polymerization reaction can depend on the process employed, but it is generally between 40° C. and 100° C. and, more particularly, the copolymerization reaction is carried out at the reflux temperature of the reaction mixture. The time of polymerization is generally between 3 and 24 hours.

According to the present invention, it is also possible by using a chain transfer agent, commonly known as a polymerization regulator, to limit the degree of polymerization of the copolymers. Representative polymerization regulators include, for example, aldehydes, such as acetaldehyde, propionaldehyde or butyraldehyde, or tertiary amines and the like.

The polymerization initiator employed in the process of the present invention, i.e. bis(4-tert. butyl cyclohexyl)peroxydicarbonate has the formula 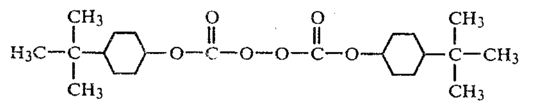 having a molecular weight of 398.5. This polymerization initiator is sold by Akzo Chemie under the trade name "Perkadox 16".

Representative unsaturated carboxylic acids which provide units (Ia) of polymer (I) include, particularly, crotonic acid, allyloxyacetic acid, allyloxypropionic acid and vinyl acetic acid.

Representative unsaturated esters which provide units (Ib) of polymer (I) include, particularly, the vinyl esters of the following acids: propionic, butyric, hexanoic, octanoic, decanoic, lauric, myristic, palmitic, stearic, 2-ethyl hexanoic, 2,2-dimethyl propanoic, 2,2-dimethyl hexanoic, 2,2-dimethyl decanoic, 2,2-dimethyl octanoic, 2,2,4,4-tetramethyl valeric, 2-isopropyl-2,3-dimethyl butyric, 2-methyl-2-ethyl heptanoic, 2-methyl-2-propyl hexanoic, 2-methyl-2-isopropyl hexanoic, 3,5,5-trimethyl hexanoic acids and the isomers thereof as well as mixtures of certain ones of these various acids and, principally, the mixture sold by Shell under the commercial name of Versatic Acid, and mixtures sold by Ugine-Kulmann under the trade names CEKANOIC $C_8$, $C_9$ and $C_{10}$, and the allyl and methallyl esters of the acids listed above and of acetic acid.

As can be seen from formula (I) of the copolymers prepared in accordance with the present invention, the copolymers can be bipolymers of vinyl acetate and an unsaturated carboxylic acid and, principally, the copolymer of vinyl acetate (85–95 weight percent)—crotonic acid (5–15 weight percent), or terpolymers or higher polymers where the polymerization involves the use of at least one other monomer in addition to vinyl acetate and the unsaturated carboxylic acid.

The present invention also relates to an aerosol hair lacquer composition containing as the lacquering resin at least one copolymer of formula I obtained by the process of the present invention, an alcohol and an aerosol propellant.

When the aerosol propellant of the aerosol hair lacquer composition is a liquified gaseous hydrocarbon such as propane, butane or isobutane or a mixture thereof, the alcohol concentration in the aerosol container is preferably lower than or equal to 65 weight percent based on the total weight of the ingredients.

On the other hand, when the aerosol propellant is a fluorinated hydrocarbon such as a "Freon" and preferably a mixture of "Freons", principally, a Freon 11/Freon 12 mixture, the alcohol concentration in the aerosol container is preferably lower than or equal to 10 weight percent based on the total weight of the ingredients.

The aerosol hair lacquer composition of the present invention can also contain a third solvent in an amount between 5 and 35 weight percent. As the third solvent, there can be employed, for example, methylene chloride, trichloroethane, ethyl chloride, acetone or ethyl acetate.

However, when a third solvent is used, the alcohol concentration depends, as before, on the nature of the aerosol propellant employed.

Thus, if the aerosol propellant of the aerosol hair lacquer composition is a liquified gaseous hydrocarbon or a mixture thereof, the alcohol concentration in the aerosol container is preferably lower than or equal to 40 weight percent based on the total weight of the ingredients.

If, on the other hand, the aerosol propellant of the aerosol hair lacquer composition is a liquified gaseous fluorochlorinated hydrocarbon, the alcohol concentration in the aerosol container is preferably lower than or equal to 8 weight percent based on the total weight of the ingredients.

In accordance with the present invention, the aerosol hair lacquer composition contains at least one copolymer prepared in accordance with the process of this invention in an amount between 0.5 and 5 weight percent relative to the total weight of the composition and preferably between 1 and 4 weight percent.

In a preferred embodiment of the present invention, the copolymers are employed in these compositions in the form of their salts which result from the neutralization of their free carboxylic acid functions using a mineral or organic base.

Representative bases include, for instance, sodium hydroxide, potassium hydroxide, ammonium hydroxide, ethanolamine, monoisopropanolamine, 2-amino-2-methyl propanol-1 and 2-amino-2-methyl-1,3-propanediol.

The bases, or mixtures thereof, are preferably used in most cases in an amount corresponding to 50-150 percent of the amount required for neutralizing the totality of the carboxylic acid functions of the copolymer.

Moreover, the aerosol hair lacquer compositions of the present invention can also contain other conventional components such as perfumes, dyes, restructuring agents, plasticizers and the like.

The following non-limiting examples are given to illustrate the process of the present invention as well as aerosol hair lacquer compositions containing copolymers prepared by this process.

EXAMPLE 1

Preparation of vinyl acetate (92 weight percent)—crotonic acid (8 weight percent) copolymer Into a 250 cc round bottom flask fitted with a condenser, a mechanical stirrer and a nitrogen lead-in tube, there are introduced 92 g of vinyl acetate, 8 g of crotonic acid, 3 g of bis(4-tert. butyl cyclohexyl)peroxydicarbonate ("Perkadox 16") and 200 g of a 1.2% aqueous solution of a suspension agent sold by Union Carbide under the trade name "Cellosize WP-09".

The reaction mixture is then brought to reflux with agitation in a 30 minute period and is subsequently maintained at reflux of the vinyl acetate-water azeotrope for 6 hours.

After cooling, the polymer is recovered in pearl form and then dried under reduced pressure.

The resulting polymer has an acid index of 53 and a viscosity of 2.34 centipoises (measured in a 5% dimethyl formamide solution at 34.6° C.).

EXAMPLE 2

Preparation of vinyl acetate (87 weight percent)—crotonic acid (8 weight percent)—vinyl stearate (5 weight percent) copolymer Into a 250 cc round bottom flask fitted with a condenser, a mechanical stirrer and a nitrogen lead-in tube, there are introduced 87 g of vinyl acetate, 8 g of crotonic acid, 5 g of vinyl stearate, 1.8 g of bis(4-tert. butyl cyclohexyl)peroxydicarbonate and 200 g of a 1.2% aqueous solution of "Cellosize WP-09" as the suspension agent.

The reaction mixture, heated to reflux with agitation in a 30-minute period, is then maintained at reflux for about 7 hours.

The polymer is then recovered in pearl form, washed and dried under reduced pressure.

The resulting polymer has an acid index of 52.3 and a viscosity of 2.97 centipoises (measured in a 5% dimethylformamide solution at 34.6° C.).

EXAMPLE 3

Preparation of vinyl acetate (90 weight percent)—crotonic acid (10 weight percent) copolymer Into a 1 liter reactor fitted with a stirrer, a condenser, a nitrogen lead-in tube, a thermometer and a reactant lead-in funnel, there are introduced 200 g of absolute ethanol containing 6 g of bis(4-tert. butyl cyclohexyl)peroxydicarbonate. This material is then heated to 60° C. There is then introduced through the reactant lead-in funnel, over a 4-hour period and with agitation, a mixture of 20 g of crotonic acid, 180 g of vinyl acetate and 4 g of bis(4-tert. butyl cyclohexyl)peroxydicarbonate. The reactant mixture in the funnel is maintained at a temperature of 5°–15° C. so as to avoid any risk of polymerization.

During the reactant addition, the internal temperature of the reactor is maintained between about 60°–65° C. At the end of the reactant introduction the reactor contents are maintained for 1 hour at this same temperature, i.e. 60°–65° C. and then for 3 hours at 75° C.

After cooling to about 20° C., the polymer is precipitated in 20 volumes of hexane. The polymer is dried under a vacuum at 20° C. The resulting polymer has an acid index of 71 and a viscosity of 1.13 centipoises (measured in a 5% dimethylformamide solution at 34.6° C.).

EXAMPLES OF AEROSOL HAIR LACQUER COMPOSITIONS

EXAMPLE A

An aerosol hair lacquer composition in accordance with the present invention is prepared by admixing the following components:

| | |
|---|---|
| Polymer obtained in accordance with Example 1 | 2 g |
| 2-amino-2-methyl propanol-1, sufficient for pH = 7, | |
| Ethanol | 7.8 g |
| Aerosol propellant: | |
| 61.5% of trichlorofluoromethane (Freon 11) | |
| 38.5% dichlorodifluoromethane (Freon 12) | |
| sufficient for | 100 g |

EXAMPLE B

An aerosol hair lacquer composition in accordance with the present invention is prepared by admixing the following components:

| | |
|---|---|
| Polymer prepared in accordance with Example 1 | 2.5 g |
| 2-amino-2-methyl propanol-1, sufficient for pH = 7 | |
| Ethanol | 4.40 g |
| Methylene chloride | 13.8 g |
| Aerosol propellant: | |
| 50% trichlorofluoromethane (Freon 11) | |
| 50% dichlorodifluoromethane (Freon 12), | |
| sufficient for | 100 g |

EXAMPLE C

An aerosol hair lacquer composition in accordance with the present invention is prepared by admixing the following components:

| Polymer prepared in accordance with Example 2 | 2 g |
| --- | --- |
| 2-amino-2-methyl propanol-1, sufficient for pH = 7 | |
| Ethanol | 7.8 g |
| Aerosol propellant: | |
| 61.5% trichlorofluoromethane (Freon 11) 38.5% dichlorodifluoromethane (Freon 12) sufficient for | 100 g |

EXAMPLE D

An aerosol hair lacquer composition in accordance with the present invention is prepared by admixing the following components:

| Polymer prepared in accordance with Example 3 | 2.5 g |
| --- | --- |
| 2-amino-2-methyl propanol-1, sufficient for pH = 7 | |
| Ethanol | 4.40 g |
| Methylene chloride | 13.8 g |
| Aerosol propellant: | |
| 50% trichlorofluoromethane (Freon 11) 50% dichlorodifluoromethane (Freon 12), sufficient for | 100 g |

EXAMPLE E

An aerosol hair lacquer composition in accordance with the present invention is prepared by admixing the following components:

| Polymer prepared in accordance with Example 3 | 3 g |
| --- | --- |
| 2-amino-2-methyl propanol-1, sufficient for pH = 7 | |
| Ethanol | 37 g |
| Methylene chloride | 20 g |
| Aerosol propellant: | 40 g |
| 35% propane 65% butane | |

EXAMPLE F

An aerosol hair lacquer composition in accordance with the present invention is prepared by admixing the following components:

| Polymer prepared in accordance with Example 3 | 3 g |
| --- | --- |
| 2-amino-2-methyl propanol-1, sufficient for pH = 7 | |
| Ethanol | 64 g |
| Aerosol propellant: | 33 g |
| 35% propane 65% butane | |

To illustrate that the polymers obtained by the process of the present invention, i.e. a polymerization reaction employing, as the polymerization initiator, bis(4-tert. butyl cyclohexyl)peroxydicarbonate, exhibit improved aerosol propellant solubility characteristics, a vinyl acetate (92 weight percent)—crotonic acid (9 weight percent) copolymer, hereinafter referred to as Polymer A, obtained with the aid of a known polymerization initiator, i.e. benzoyl peroxide, is compared to a polymer, prepared from the same monomers, and, hereinafter referred to as Polymer B, but which has been obtained with the aid of bis(4-tert. butyl cyclohexyl)-peroxydicarbonate as the polymerization initiator.

A. Preparation of Polymer A using benzoyl peroxide

Into a 250 cc round bottom flask fitted with a condenser, a mechanical stirrer and a nitrogen lead-in tube, there are introduced 92 g of vinyl acetate, 8 g of crotonic acid, 4 g of benzoyl peroxide and 200 g of a 1.2% aqueous solution of a suspension agent sold under the trade name "Cellosize WP-09".

The reaction mixture is heated to reflux with agitation in a 30-minute period and then maintained at the reflux of the vinyl acetate-water azeotrope for about 6 hours.

The polymer is then recovered in pearl form, washed and dried under reduced pressure.

The resulting polymer has an acid index of 54, and a viscosity of 2.20 centipoises (measured in a 5% solution of dimethylformamide at 34.6° C.).

B. Polymer B, used for the comparative test, set forth below, is that prepared in accordance with Example 1 given above The sole significant difference between the process for producing Polymer A and the process for producing Polymer B resides in the nature of the polymerization initiator employed which, in the case of preparing Polymer A is benzoyl peroxide and in the case of preparing Polymer B is bis(4-tert. butyl cyclohexyl)peroxydicarbonate.

It will be recognized, however, that the polymerization times and amounts of polymerization initiator employed in the respective processes for producing Polymer A and Polymer B vary somewhat. However, such variations have been considered necessary so as to obtain polymers having comparable viscosities.

Various methods can be employed to demonstrate the solubility of a copolymer in a mixture of two liquids, one of which is a solvent for the copolymer, the other being a precipitant for the copolymer.

One of these methods involves dissolving a given quantity of the copolymer in a given amount of solvent and then slowly introducing the precipitant, with agitation, at a predetermined temperature, up to the point of incipient cloudiness or turbidity.

The amount of precipitant necessary to cause this incipient cloudiness constitutes a measure of the solubility of the copolymer in the given system of solvent-precipitant.

Thus it can be seen that the greater the amount of precipitant required for incipient cloudiness or turbidity, the greater is the solubility of copolymer in the system.

For each of Polymers A and B, the following methods for evaluating their respective solubilities have been used:

1. In an aerosol container there are introduced 10 g of an ethanolic solution containing 2 g of polymer and that amount of 2-amino-2-methyl propanol-1 required to neutralize the free carboxylic acid functions of the polymer. A valve without a plunger tube is seated and there is introduced at 20° C. a propellant mixture consisting of 61.5% trichlorofluoromethane (Freon 11) and 38.5% dichlorodifluoromethane (Freon 12).

2. In an aerosol container there are introduced 8 g of ethanol, 25 g of methylene chloride, 2.5 g of polymer and that amount of 2-amino-2-methyl propanol-1 required to neutralize the free carboxylic acid functions of the polymer. A valve without a plunger tube is seated and there is introduced at 20° C. a propellant mixture consisting of 50% trichlorofluoromethane (Freon 11) and 50% dichlorodifluoromethane (Freon 12).

For each of the containers containing, on the one hand, Polymer A, and on the other hand, Polymer B, the weight of the propellant mixture introduced to obtain incipient cloudiness or turbidity is recorded.

The results obtained are set forth in the following table:

|  | Amount of propellant mixture (g) to obtain incipient cloudiness in the system | |
|---|---|---|
|  | Method 1 | Method 2 |
| Polymer A | 63 | 156 |
| Polymer B | 91 | 182 |

It can be seen that the use of Polymer B, i.e. the polymer obtained in accordance with the present invention, permits, for the same amount of alcohol or mixture of alcohol and methylene chloride, the use of more significant amounts of the aerosol propellant before incipient cloudiness occurs.

These tests establish the improved solubility characteristics of Polymer B in the propellant, which permits then a reduction in the amount of alcohol necessary to achieve a good aerosol hair lacquer composition.

An excellent aerosol hair lacquer composition using Polymer B can be prepared using the following amounts of components:

| Polymer B | 2 g |
|---|---|
| 2-amino-2-methyl propanol-1, sufficient for pH = 7 | |
| Ethanol | 7.8 g |
| Aerosol propellant: | |
| 61.5% Freon 11 | |
| 38.5% Freon 12, | |
| sufficient for | 100 g |

On the other hand, the use of Polymer A rather than Polymer B in the above aerosol hair lacquer composition, necessitates the use of 11 g of ethanol to obtain a good aerosol lacquer, that is good solubilization of the polymer in the solvent-precipitant system.

The "static holding" property of the aerosol hair lacquer compositions produced with Polymer A and Polymer B has also been studied.

The "static holding" characteristic of such a hair lacquer composition is determined in the following manner:

Samples of 50 hairs, 25 cm in length, are rolled around an 8-mm diameter roller. The rollers are mounted on a device permitting their rotation about their axis at a speed of 1 turn per second. The rolled up samples receive an application of lacquer for 10 seconds and are then dried with free air for 2 hours. Finally, the samples are removed from the rollers and placed in a tank wherein the relative humidity is 80% and the temperature is 25° C. The samples unroll as a function of time and their released length, after two hours, furnishes the "static holding" value of the tested lacquer.

Various aerosol lacquers have been tested using varying Polymer A and Polymer B concentrations. It has surprisingly been noted that equal "static holding" values are achieved when using 2.25 g of Polymer A in an aerosol lacquer composition and when using 2 g of Polymer B in an otherwise essentially identical aerosol hair lacquer composition.

These tests illustrate that the use of Polymer B, obtained by the process of the present invention, makes it possible to use a lesser amount of resin while still achieving an essentially identical "static holding" value.

What is claimed is:

1. A process for preparing a copolymer useful in cosmetics, in particular, for the production of aerosol hair lacquer compositions, comprising copolymerizing in the presence of bis(4-tert. butyl cyclohexyl)peroxydicarbonate, as the polymerization initiator, 85–95 weight percent vinyl acetate and 5–15 weight percent crotonic acid.

2. The process of claim 1 wherein the copolymerization is carried out in mass, in suspension in an inert solvent, in solution in a solvent or in emulsion.

3. The process of claim 1 wherein the copolymerization is carried out in suspension in water in the presence of a protective colloid, the resulting copolymer being obtained in pearl form.

4. The process of claim 1 wherein said bis(4-tert. butyl cyclohexyl)peroxydicarbonate is employed in an amount of 0.5–5 weight percent based on the total weight of the monomers being reacted.

5. The process of claim 1 wherein the polymerization is carried out at a temperature between 40° and 100° C.

6. The process of claim 1 wherein the polymerization is carried out at the reflux temperature of the reaction mixture.

* * * * *